US009381490B2

(12) United States Patent
Kleijn

(10) Patent No.: US 9,381,490 B2
(45) Date of Patent: Jul. 5, 2016

(54) PROCESS AND APPARATUS FOR THE PRE-TREATMENT OF BIOMASS

(75) Inventor: Aart Berthold Kleijn, Cartagena (ES)

(73) Assignee: HRS INVESTMENTS LIMITED, Herts (GB)

(*) Notice: Subject to any disclaimer, the term of this patent is extended or adjusted under 35 U.S.C. 154(b) by 878 days.

(21) Appl. No.: 13/504,583

(22) PCT Filed: Apr. 14, 2010

(86) PCT No.: PCT/ES2010/070226
§ 371 (c)(1),
(2), (4) Date: Jun. 19, 2012

(87) PCT Pub. No.: WO2011/051518
PCT Pub. Date: May 5, 2011

(65) Prior Publication Data
US 2012/0264071 A1    Oct. 18, 2012

(30) Foreign Application Priority Data

Oct. 27, 2009 (ES) .................................. 200930913

(51) Int. Cl.
*F27D 13/00* (2006.01)
*F28D 15/00* (2006.01)
(Continued)

(52) U.S. Cl.
CPC .. *B01J 19/24* (2013.01); *C10L 5/44* (2013.01); *C10L 9/086* (2013.01); *C12M 45/06* (2013.01);
(Continued)

(58) Field of Classification Search
CPC .......... C10L 9/086; C10L 5/44; C12M 45/06; C12M 45/20; C13K 1/02; Y02E 50/10; Y02E 50/30

USPC ............. 432/12, 9, 11, 18; 435/165; 585/240; 165/104.13; 42/520, 521, 522, 42/506–511
See application file for complete search history.

(56) References Cited

U.S. PATENT DOCUMENTS 4,908,067 A * 3/1990 Just ................................ 127/37
5,137,744 A * 8/1992 Cagley et al. ................. 426/615
(Continued)

FOREIGN PATENT DOCUMENTS

EP    0 617 897 A1    10/1994
ES    2 054 996 T3    8/1994
(Continued)

OTHER PUBLICATIONS http://www.hrs-heatexchangers.com/en/applications/biofuels/thermal-hydrolysis-biomass-biofuel-bioethanol-biogas-3-3.aspx, "Thermal hydrolysis for second generation biofules", HRS, Jul. 6, 2009, pp. 1-3.*

(Continued)

*Primary Examiner* — Steven B McAllister
*Assistant Examiner* — Steven Anderson, II
(74) *Attorney, Agent, or Firm* — Ostrolenk Faber LLP

(57) ABSTRACT

A process for pretreatment of biomass and an installation for practicing the process, the process including, as well, the subsequent biological treatment and obtaining of biofuel from the biomass. The process is based on the use of at least one scraped surface exchanger and comprises the following steps: heating the biomass to a temperature equal to or lower than 110° C. in an exchanger; further heating the heated biomass so obtained to a temperature between 150 and 175° C. in a scraped surface exchanger; thermal hydrolyzing the biomass at a temperature between 150 and 175° C; and cooling the thermal hydrolyzed biomass for the subsequent biological treatment thereof.

3 Claims, 2 Drawing Sheets

(51) Int. Cl.
   *B01J 19/24* (2006.01)
   *C10L 5/44* (2006.01)
   *C10L 9/08* (2006.01)
   *C12M 1/00* (2006.01)
   *C13K 1/02* (2006.01)

(52) U.S. Cl.
   CPC .............. *C12M 45/20* (2013.01); *C13K 1/02* (2013.01); *B01J 2219/24* (2013.01); *Y02E 50/10* (2013.01); *Y02E 50/30* (2013.01)

(56) References Cited

U.S. PATENT DOCUMENTS

| | | | | |
|---|---|---|---|---|
| 5,411,594 | A * | 5/1995 | Brelsford | 127/37 |
| 5,443,857 | A * | 8/1995 | Arph et al. | 426/522 |
| 6,326,461 | B1 * | 12/2001 | Giroux et al. | 530/200 |
| 2004/0168990 | A1 * | 9/2004 | Solheim | C02F 1/025 210/774 |
| 2008/0064906 | A1 * | 3/2008 | Foody et al. | 585/242 |

FOREIGN PATENT DOCUMENTS

| | | |
|---|---|---|
| ES | 2 158 752 A1 | 9/2001 |
| ES | 2 228 530 T3 | 4/2005 |
| WO | WO 94/24316 A1 | 10/1994 |
| WO | WO 96/09882 | 4/1996 |
| WO | WO 00/73221 A1 | 12/2000 |
| WO | WO 2006/034590 A1 | 4/2006 |
| WO | WO 2008/026932 A1 | 3/2008 |

OTHER PUBLICATIONS

Carter Fox, Chemical and Thermal Characterization of Three Industrial Lignins and Their Corresponding Lignin Esters, May 2006, p. 56 (Table 3.3).*

Nathan Mosier et al., "Features of Promising Technologies for Pretreatment of Lignocellulosic Biomass," Bioresource Technology, vol. 96, No. 6 (2005), pp. 673-686.

International Search Report dated Jul. 22 2010 issued in connection with corresponding international patent application No. PCT/ES2010/070226.

Extended European Search Report containing the Supplementary, European Search Report and European Search Opinion dated May 22, 2015 in corresponding European Patent Application No. EP 10 82 6139 (10 pages).

SPX: "Scraed Surface Heat Exchangers for Industrial Duty," Votator® II 4 x 120, Votator® II Extra Heavy Duty, Waukesha Cherry-Burrell, an SPX Brand, Apr. 2008, retrieved from the Internet: URL:http:/www.intec-as.dk/fileadmin/images/Waukesha/Votator. pdf [retrieved on May 12, 2015], (12 pages).

U.S. Appl. No. 14/621,882, filed Feb. 13, 2015 in the name of Aart Berthold Klein entitled "Process and Apparatus for the Pre-Treatment of Biomass."

Written Opinion of the International Searching Authority with English language translation in corresponding International Application No. PCT/ES2010/070226 (13 pages).

* cited by examiner

PROCESS AND APPARATUS FOR THE PRE-TREATMENT OF BIOMASS

CROSS REFERENCE TO RELATED APPLICATIONS

The present application is a 35 U.S.C. §371 National Phase conversion of PCT/ES2010/070226, filed Apr. 14, 2010, which claims benefit of Spanish Application No. P200930913, filed Oct. 27, 2009, the disclosures of which are incorporated herein by reference.

FIELD OF THE INVENTION

The present invention relates to a process and installation for the pretreatment of biomass coming from any organic material source. The pretreated biomass can then be subjected to biological treatment for the production of bioethanol or biogas.

BACKGROUND OF THE INVENTION

For obtaining biofuels from biomass it is necessary for bacteria and enzymes to attack the hemicellulose and cellulose thereof to transform them into bioethanol or biogas. Hemicellulose and cellulose are protected by lignin, a fiber enveloping them and preventing said biological attack. Therefore the first step for obtaining biofuel is to pretreat the biomass to break the lignin and to make the hemicellulose and cellulose accessible to the bacteria and enzymes.

It is known in the state of the art that treatment of organic material at a temperature comprised between 160-240° C. causes the hydrolysis of a significant part of the organic material, therefore a process for thermal pretreatment of organic wastes, wood, etc has been developed. In the case of obtaining biofuels which currently form an important alternative to fossil fuels, a pretreatment of the biomass to be used considerably increases the conversion to the same which is of great economic and industrial interest.

Various processes for the pretreatment of biomass which are classified into chemical and thermal pretreatments are known, among which the process of vapor explosion which can be carried out in a conventional flash tank must be highlighted. In this sense WO96/09882 describes a pretreatment of biomass to break the lignin, based on the thermal explosion which consists of subjecting the biomass to heating and high pressure for suddenly releasing the pressure whereby the water retained inside the biomass explodes, breaking the lignin barrier and releasing the hemicellulose and cellulose on which bacteria and enzymes can then act. However, among other drawbacks, this process is not a continuous process and only around 50% of the invested energy is recovered in the process for pretreatment whereby the resulting energy balance is poor and the energy consumption needed to produce bioethanol or biogas is high.

Therefore and due to the increasing interest in biofuels, the need in the state of the art to provide an alternative process for the pretreatment of biomass which is efficient from an energy point of view and is therefore interesting to put it into practice at the industrial level continues to exist.

DETAILED DESCRIPTION OF THE INVENTION

The invention is described in detail below referring to FIGS. 1 and 2.

In a first aspect, the invention relates to a new process for the pretreatment of biomass comprising the following steps:
 a) heating the biomass to a temperature equal to or lower than 110° C. in an exchanger H1;
 b) heating the biomass obtained in step a) to a temperature comprised between 150 and 175° C. in a scraped surface exchanger H2;
 c) thermal hydrolyzing the biomass obtained in step b) at a temperature comprised between 150 and 175° C.; and
 d) cooling the thermal hydrolyzed biomass for the subsequent biological treatment thereof.

The biomass used in the process is previously grinded and can come from any organic material source, for example, plant wastes, wood, etc., and is initially at room temperature of around 20° C.

Figure 1:
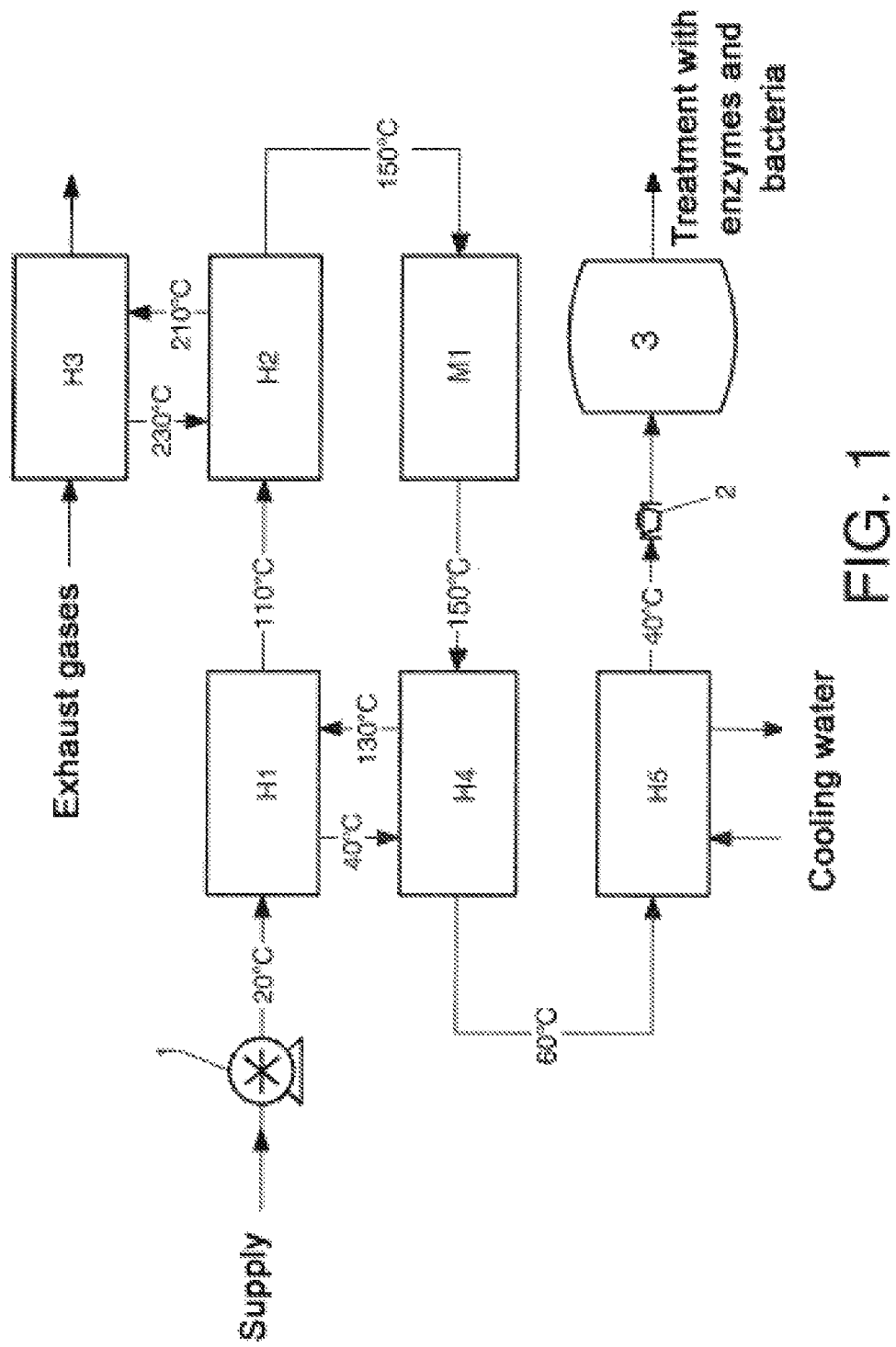
FIG. 1 shows a flow chart of a particular embodiment of the process of the invention and a particular embodiment of the installation of the invention to put it into practice.

In a particular embodiment of the process of the invention which is outlined in FIG. 1, step a) is performed in an exchanger H1 in which the biomass reaches a temperature of around 110° C. It is important to control this temperature at the outlet of H1. The heat needed for this step a) comes from the hot water generated in a scraped surface exchanger H4. The hot water, generally at 130° C. is conducted by suitable means from H4 to H1. Once the heat is transferred to the biomass, the water cooled to 40° C. returns from H1 to H4.

The biomass at 110° C. is then carried to a scraped surface exchanger H2 where step b), according to which it is heated until reaching a temperature comprised between 150 and 175° C., takes place.

Thermal oil and an exchanger H3 connected to the scraped surface exchanger H2 between which the thermal oil leaving from H3 towards H2 at 230° C. and from H2 to H3 at 210° C. circulates, is used for heating the biomass in H2. In a particular embodiment, exhaust gases produced in some other point of the installation are used for heating the thermal oil. In another particular embodiment, H2 can be alternatively heated, for example by means of vapor from a boiler thus eliminating the use of exchanger H3 in the installation of the invention.

It is important at this point to prevent the evaporation of water from the biomass, therefore a pressure comprised between 6 and 8 bar is maintained whereas the biomass is at high temperature (between 150 and 175° C.) during the process of the invention.

The biomass leaving H2 is carried to a maintenance area M1 where step c) of thermal hydrolyzing the biomass at pressure and a temperature comprised between 150 and 175° C. and during a predetermined time takes place.

The thermal hydrolyzed biomass is cooled in step d) until reaching a temperature of 60° C. in the scraped surface exchanger H4, using cooled water coming from the exchanger H1 as has been mentioned above. In a particular embodiment a water loop which allows transporting heat between H1 and H4 is used. This combination can be defined as a direct energy recovery system and contributes in an essential manner to the improved energy yield with respect to other processes of the technique.

The biomass cooled to 60° C. is continuously cooled in H4 to a temperature of 40° C. in an exchanger H5, temperature at which generally the biological processes with enzymes and bacteria take place in a suitable tank.

In this particular embodiment of the process of the invention the exchangers H1 and H5 are of conventional type, particularly of tube in tube type, whereas the exchangers H2 and H4 are scraped surface exchangers. At temperatures greater than 110° C., the use of conventional tubular exchangers would involve the need of stopping the process for cleaning and removing the internal fouling. However the use of the scraped surface exchangers H2 and H4 allows carrying out the process of the invention continuously since the wall is continuously cleaned and the optimum heat exchange thereof is further assured. Thus fouling is prevented, the operation can be continuous which improves and facilitates the process.

Figure 2:
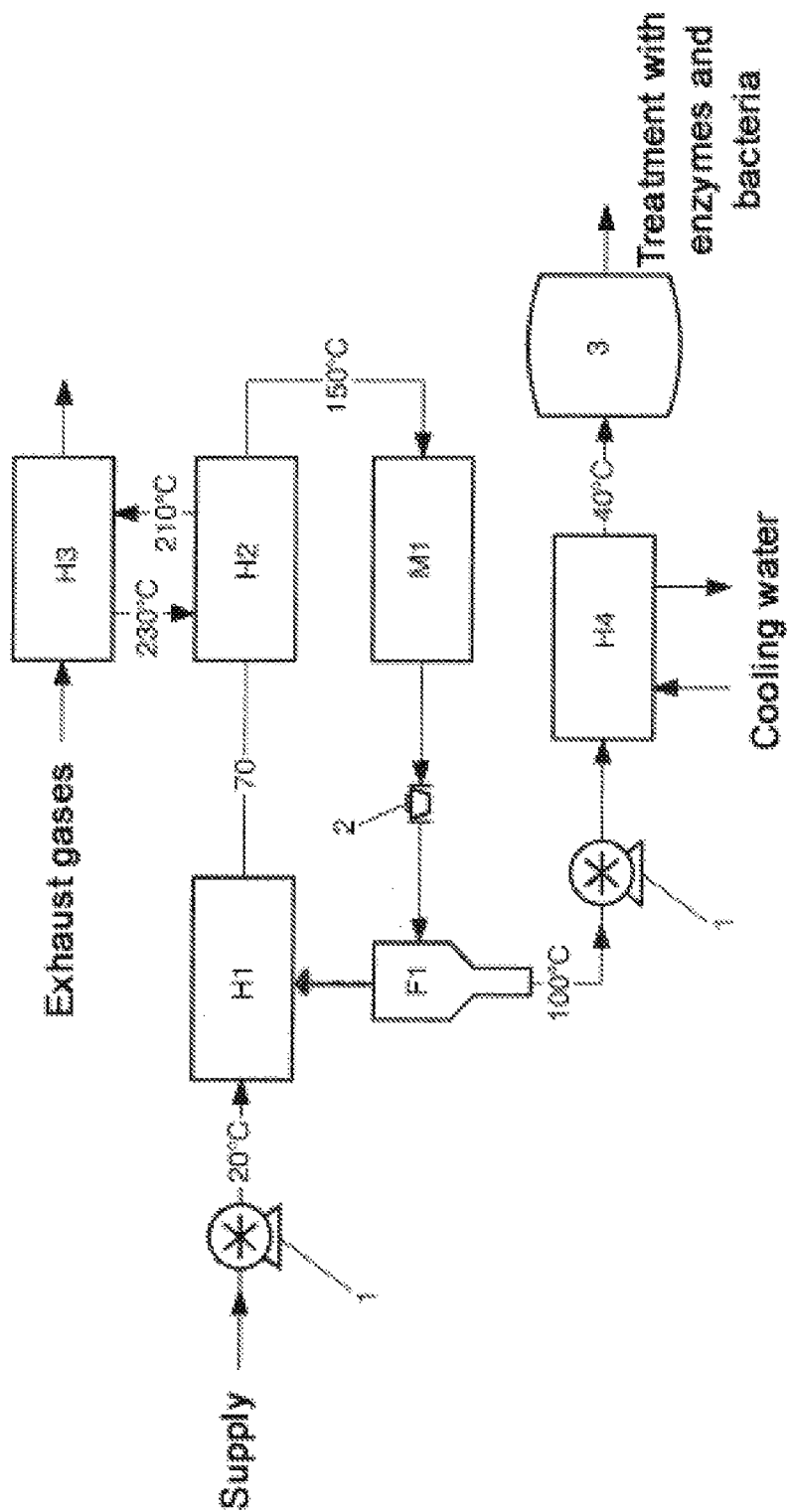
FIG. 2 shows a flow chart of a particular embodiment of the process of the invention and a particular embodiment of the installation of the invention to put it into practice.

In another particular embodiment of the process of the invention which is outlined in FIG. 2, step a) is performed in an exchanger H1 in which the biomass reaches a temperature of around 70-80° C. and in which the heat needed for the heating thereof comes from the water vapor generated at 100° C. in a flash tank F1.

The biomass at 70-80° C. is carried to the scraped surface exchanger H2 where step b) according to which it is heated to reach a temperature comprised between 150 and 175° C. takes place.

Thermal oil and an exchanger H3 connected to the scraped surface exchanger H2 between which the thermal oil leaving from H3 towards H2 heated at 230° C. and from H2 to H3 cooled to 210° C. circulates, is used for heating the biomass in H2. In a particular embodiment, exhaust gases produced in some other point of the installation are used for heating the thermal oil. In another particular embodiment, H2 can be alternatively heated, for example by means of vapor from a boiler thus eliminating the use of exchanger H3 in the installation of the invention.

It is important at this point to prevent the evaporation of water from the biomass, therefore a pressure comprised between 6 and 8 bar is maintained whereas the biomass is at high temperature (between 150 and 175° C.).

The biomass leaving H2 is carried to a maintenance area M1 where step c) of thermal hydrolyzing the biomass at pressure and at a temperature comprised between 150 and 175° C. and during a predetermined time takes place.

According to this particular embodiment of the invention, the process further comprises a vapor explosion of the thermal hydrolyzed biomass in step c) taking place in a flash tank F1. This step further reduces the particle size of the thermal hydrolyzed biomass and serves for generating heat which is used in step a). Between the thermal hydrolysis and vapor explosion, the pressure of the thermal hydrolyzed biomass is reduced to atmospheric pressure. To that end the installation is provided with a pressurized valve. The biomass enters the flash tank F1 in a radial manner and the lowering of pressure causes the evaporation of large amount of water from the biomass. Thus water vapor which is conducted at 100° C. temperature to the exchanger H1 is generated for the use thereof. In this sense the combination of H1 and F1 allows recovering a large amount of energy. The biomass is driven to the exchanger H4 from which it leaves at 40° C. for its subsequent biological treatment in a suitable tank. For this final exchange cooling water from the water system of the installation is used.

The process of the invention allows recovering a percentage comprised between 70 and 76% of the energy used for thermal hydrolyzing said organic material. Furthermore the process of the invention is based on an indirect heating using heat exchangers of which at least one of them is a scraped surface heat exchanger which allows its continuous put into practice. The process does not use chemical additives nor does it need additional water supply. In this sense the water content of the biomass is maintained such which the same amount of water as the amount obtained enters.

Another object of the present invention relates to a suitable installation to carry out the process of the invention, comprising at least one scraped surface exchanger and a combination of determined elements such as detailed below, referring to FIGS. 1 and 2 which allow obtaining a high energy balance in the process of the invention.

The installation, hereinafter installation of the invention, comprises among other elements means for supplying the biomass; at least one pump 1 driving the biomass throughout the installation, as well as means for controlling and maintaining the pumping speed, a pressurized valve 2 for maintaining the suitable pressure to carry out the process of the invention; a tank 3 for the pretreated product obtained; and means for measuring and controlling the temperatures.

The installation of the invention comprises a maintenance area M1 where the thermal hydrolysis at high temperature and pressure takes place. In a particular embodiment, this area is a long coil through which the biomass is kept circulating a determined time.

The installation of the invention also comprises at least one scraped surface exchanger for the area in which the biomass is at high temperatures of between 150 and 175° C. and which prevents fouling. This exchanger can be acquired commercially (Unicus® HRS).

In a particular embodiment the installation of the invention which is depicted in FIG. 1 comprises the following elements in series:

(i) an exchanger H1;
(ii) a scraped surface exchanger H2;
(iii) a maintenance area M1;
(iv) a scraped surface exchanger H4; and
(v) an exchanger H5.

The exchanger H1 is connected with the scraped surface exchanger H4 through means that transport cooled water from H1 to the scraped surface exchanger H4 and hot water from H4 to H1. The cooled water is at approximately 40° C. and the hot water 130° C.

In a particular embodiment, the scraped surface exchanger H2 is connected to an multitubular conventional type exchanger H3 by means that transport hot thermal oil at an approximate temperature of 230° C. towards H2 and means which allow the return of said thermal oil cooled to a temperature of approximately 210° C. The heat needed for the heating of the thermal oil comes from exhaust gases of some point of the installation. In an alternative embodiment, instead of H3 vapor from a boiler is used.

The biomass leaves H2 at high temperature comprised between 150 and 175° C., enters the maintenance area M1 where the thermal hydrolysis is carried out and then enters the scraped surface exchanger H4 where heat is exchanged with H1 such that the thermal hydrolyzed biomass leaves H4 at a temperature of approximately 60° C.

Then, the hydrolyzed biomass is cooled to 40° C. in the H5 exchanger using cooling water coming from the water system of the installation and is carried to a tank for the subsequent biological treatment thereof.

In this particular embodiment H1 and H5 are conventional tube in tube exchangers and H2 and H4 are scraped surface exchangers. Furthermore, the installation is provided with means for maintaining a pressure comprised between 6 and 8 bar within the area of the installation where the biomass is at high temperature, i.e., from the exchanger H2 to the exchanger H4 including both.

In another particular embodiment the installation of the invention (FIG. 2) comprises the following elements in series to carry out the process of the invention:
(i) an exchanger H1;
(ii) a scraped surface exchanger H2;
(iii) a maintenance area M1;
(iv) a flash tank F1; and
(v) an exchanger H4.

The installation comprises means for transporting water vapor generated at 100° C. in the flash tank F1 to the exchanger H1 where said heat is used for heating the biomass entering at approximately 20° C. to a temperature typically of 70° C.

The biomass is conducted to a connected scraped surface exchanger H2, in a particular embodiment, to a multitubular conventional type exchanger H3 by means that transport hot thermal oil at an approximate temperature of 230° C. towards H2 and means which allow the return of said thermal oil cooled to a temperature of approximately 210° C. The heat needed for heating the thermal oil comes from exhaust gases of some point of the installation. In an alternative embodiment, instead of H3 vapor from a boiler is used.

The biomass leaves H2 at a temperature between 150 and 175° C. and enters the maintenance area M1 where the thermal hydrolysis is carried out. The biomass leaving at pressure between 6 and 8 bar of M1 enters a flash tank F1 at atmospheric pressure as a result of a depressurized valve located between M1 and F1. The vapor explosion takes place in F1, generating water vapor which leaves at 100° C. towards the exchanger H1 and which is used for heating the biomass in H1 recovering energy. The thermal hydrolyzed biomass which is driven towards the exchanger H4 by means of a pump leaves F1 at 100° C.

The exchanger H4 uses cooling water coming from the water system of the installation for cooling the hydrolyzed biomass. In H4 the thermal hydrolyzed biomass is cooled and leaves at 40° C. towards a tank where the biological treatment can be carried out.

The installation, as has been previously mentioned, is provided with a pressurized valve for maintaining a pressure comprised between 6 and 8 bar within the area of the installation from the exchanger H2 included up to the inlet in the flash tank F1.

The invention claimed is:

1. A process for the pretreatment of biomass comprising the following steps:
a) heating the biomass to a temperature of no more than 110° C and at least 100° C. in a first exchanger, wherein the heat needed comes from the hot water generated in a second scraped surface exchanger;
b) heating the biomass obtained in step a) to a temperature between 150 and 175° C. in a first scraped surface exchanger at a pressure between 0.6-0.8MPa (6-8 bar);
c) thermal hydrolyzing the biomass obtained in step b) at a temperature between 150 and 175° C. at a pressure between 0.6-0.8 MPa (6-8 bar) in a maintenance area; and
d) cooling the thermal hydrolyzed biomass for the subsequent biological treatment thereof to a temperature equal to or lower than 60° C. in the second scraped surface exchanger with cooled water from the first exchanger and which is then cooled to a temperature of 40° C. in a second exchanger.

2. The process for the pretreatment of biomass according to claim 1 wherein the process further comprises providing an installation for pretreatment of the biomass, said installation:
comprising means that transport cooled water from the first exchanger to the second scraped surface exchanger and hot water from the second scraped surface exchanger to the first exchanger, and
means for maintaining a pressure between 0.6-0.8 MPa (6 and 8 bar) within the area of the installation from the first scraped surface exchanger to the second scraped surface exchanger including both, and
wherein the second exchanger uses cooling water coming from the water system of the installation for cooling the thermal hydrolyzed biomass to 40° C.

3. The process for the pretreatment of biomass according to claim 2, wherein the first scraped surface exchanger is connected with a third exchanger by means that transport thermal oil heated at 230° C. from the third exchanger to the first scraped surface exchanger and thermal oil cooled to 210° C. from the first scraped surface exchanger to the third exchanger.

* * * * *